Figure 5:
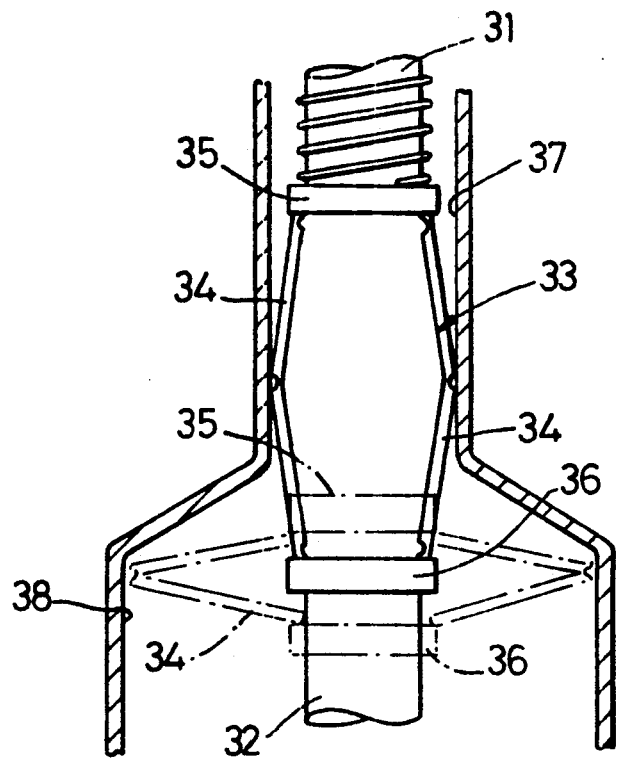

United States Patent [19]

Crossman et al.

[11] Patent Number: 5,300,030
[45] Date of Patent: Apr. 5, 1994

[54] INJECTION DEVICES

[75] Inventors: David D. Crossman, Watlington; Jeremy Marshall, Jericho; Ernest J. Mumford, Witney, all of England

[73] Assignee: Owen Mumford Limited, Oxford, United Kingdom

[21] Appl. No.: 890,131

[22] Filed: May 29, 1992

[30] Foreign Application Priority Data

May 30, 1991 [GB] United Kingdom ............. 911600

[51] Int. Cl.$^5$ .................................................. A61M 5/20
[52] U.S. Cl. ........................................ 604/136; 604/134; 604/156; 604/157; 604/192; 604/232
[58] Field of Search ............... 604/95, 110, 130–136, 604/138–139, 156–158, 192–196, 198–206, 218, 232; 128/D 1; 606/172, 182

[56] References Cited

U.S. PATENT DOCUMENTS 3,306,290  2/1967  Weltman ........................... 604/201
4,998,922  3/1991  Kuracina et al. .

FOREIGN PATENT DOCUMENTS 728248  4/1955  United Kingdom .

Primary Examiner—Randall L. Green
Assistant Examiner—A. Zuttarelli
Attorney, Agent, or Firm—Young & Thompson

[57] ABSTRACT

An injection device has a needle (22) which, when the device is operated, is first caused to project, then liquid is forced out through it, and finally the needle is automatically retracted. The needle (22) extends forwardly from a capsule (18) that can slide longitudinally within a barrel-like body (1), a relatively weak spring (19) normally maintaining the capsule and needle retracted. A more powerful spring (14) acts oppositely on a plunger (26) which, when released, shoots the capsule forward by acting on the liquid therein, and then forces the liquid out through the projecting needle (22). At the end of the forward stroke the plunger (26) and capsule (18) are decoupled and the weak spring (14) returns the exhausted capsule and its needle to the retracted position.

7 Claims, 3 Drawing Sheets

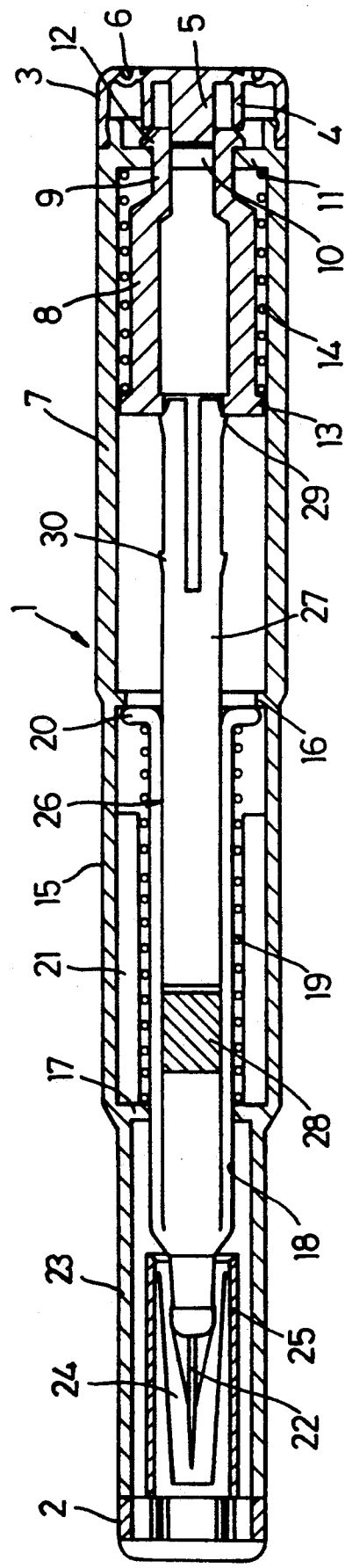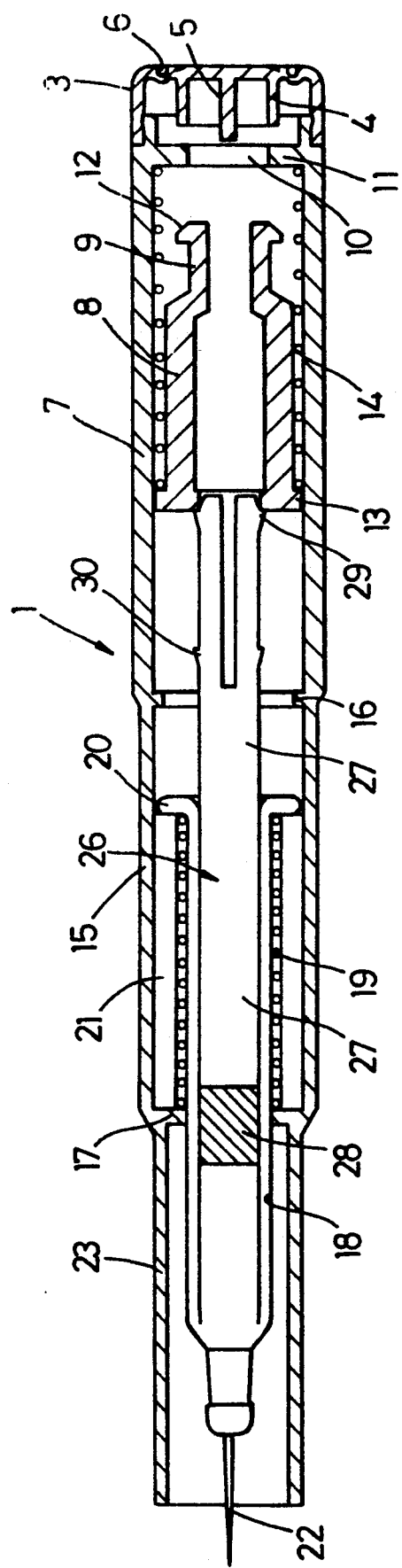
Fig. 1
Fig. 2

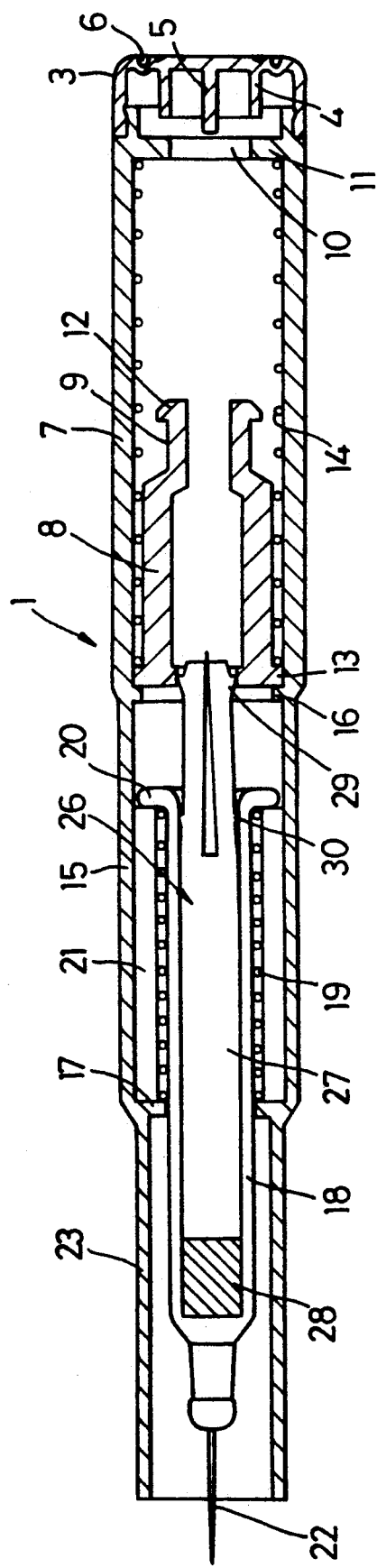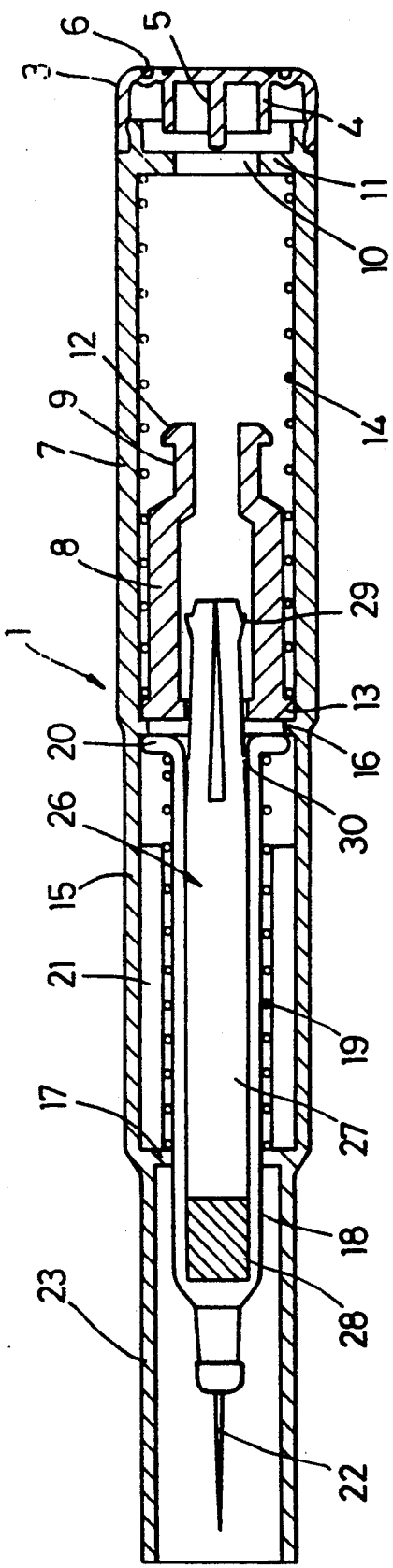

INJECTION DEVICES

This invention relates to injection devices, and in particular medical ones where the needle is retracted and thus made safe after use.

Such injection devices are in increasing demand for obvious reasons. There is great danger in a discarded syringe with a possibly infected needle. It is highly desirable that retraction of the needle after use should not only be possible but also be automatic. It should not rely on the user making it safe by some manipulation which can all too easily be overlooked. Also, with the increasing use of self-administered drug therapy, there is a demand for a device whereby the syringe needle is not normally visible to the user before or after the injection.

It is the aim of this invention to provide a device which meets these requirements.

According to the present invention there is provided an injection device comprising a barrel, a spring loaded drive member therein, release mechanism for allowing said member to be sprung forwardly within the barrel, a spring loaded, charged capsule having a needle initially in a retracted position at the forward end of the barrel, the spring loading of the capsule being in opposition to but weaker than the spring loading of said drive member, a plunger with which the forward end of said drive member cooperates, and means for decoupling the plunger from said drive member at the end of the forward stroke, the arrangement being such that said forward stroke first drives the capsule to a needle projecting position, said drive member acting through the plunger and the capsule charge, and secondly forces the plunger to eject said charge through the needle, the capsule spring loading being then freed by the decoupling means to return the capsule to the needle retracted position.

The capsule will conveniently be a proprietary syringe with its plunger removed and replaced by said plunger which co-operates with said drive member.

Preferably, the spring loading provided will be by coil springs co-axial within the barrel.

In one form, the decoupling means is provided by the rear end of said plunger which is abutted by said drive member and which is adapted to be deformed when it comes into co-operation with the capsule. For example, the rear end of the plunger may be bifurcated and there may be exterior projections on the fingers formed thereby, said projection when engaged by the capsule on entry therein causing the fingers to be wedged together and in this constricted condition to be free to enter a passage within the drive member.

In an alternative arrangement, the decoupling means may be provided by a thrust device between the rear end of the plunger and the forward end of the drive member, and a contoured passage within the barrel, the thrust device being maintained effectively rigid by confinement within a narrow portion of said passage for all but the final stage of the forward stroke, but being rendered non-rigid when the confinement is eased by a wide portion of said passage for said final stage. One example of such a thrust device is an element such as a ball that rolls free or otherwise escapes from between the plunger and the drive member when it attains the freedom of said wide portion. Another possible thrust device is a hinged linkage which is maintained substantially straight and extended by said narrow portion but which collapses sideways when it attains the freedom of said wide portion.

The drive member will generally have a catch which initially is engaged with the barrel, holding the forward spring energised. The release mechanism, which may be a button-like rear end cap, frees this catch.

Figure 6:
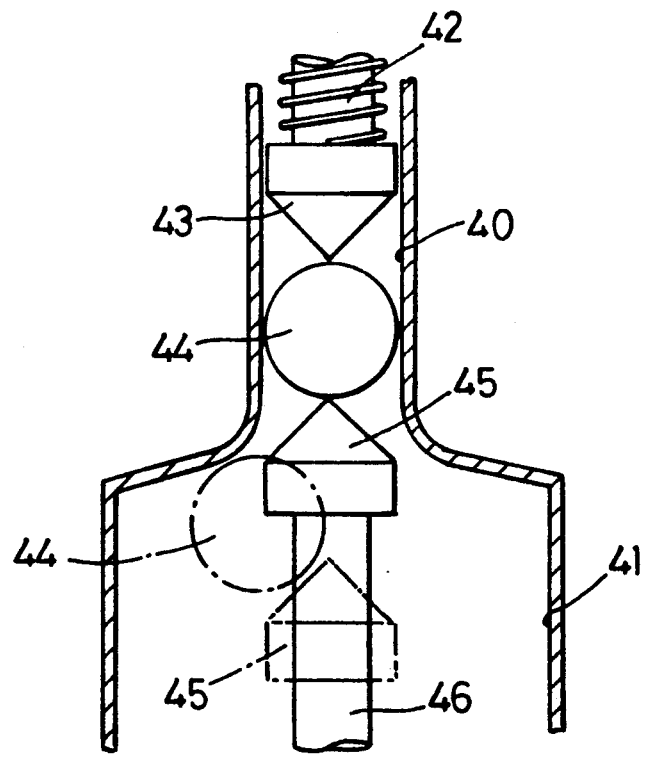

For a better understanding of the invention, some embodiments will now be described, by way of example, with reference to the accompanying drawings, in which:

FIGS. 1–4 are longitudinal sections of an injection device in progressive stages of operation, FIG. 5 is a sectional detail of an alternative injection device, and FIG. 6 is a sectional detail of a third injection device.

The injection device of FIGS. 1 to 4 has a stepped barrel 1 reducing towards the forward end where there is a cap 2 which is removed for use. At the rear end there is a cap 3 which is snapped on by its peripheral flange and which has an inner annulus 4 and a central tab 5. The cap 3 is rotatable on the barrel 1 and its central portion can be flexed inwards, axially of the barrel, by virtue of an annular weakness 6 near the periphery.

The largest diameter portion 7 of the barrel houses a bottle shaped drive member 8 whose neck is towards the rear and which has a central aperture in its base. The neck 9 is bifurcated and extends through an aperture 10 defined by an inwardly extending flange 11. Beyond that flange the drive member 8 terminates in out-turned hooks with bevelled surfaces 12 with which the annulus 4 cooperates. At the other, forward end of the drive member 8, there is an outward flange 13, and a coil spring 14 surrounding the member acts between this and the flange 11. As shown in FIG. 1, with the drive member 8 captive to the rear of the barrel, this spring is at its maximum compression.

The transition between the rear portion 7 and the intermediate portion 15 of the barrel 1 is internally defined by an annular rib 16. At the forward end of this portion 15 there is another annular rib 17 and initially a charged capsule 18 is located by these ribs, a surrounding coil spring 19 reacting against the rib 17 and urging a flange 20 at the rear of the capsule against the rib 16. The spring 19 is somewhat weaker than the spring 14 and the forward travel of the capsule, when this spring 19 becomes compressed, is limited by spacers 21 extending rearwardly from the rib 17 to provide an abutment for the flange 20.

The leading portion of the capsule 18, with a needle 22, is located in the forward end portion 23 of the barrel, the tip of the needle being set back from the end. Initially, the needle 22 is sheathed in a self-sealing silicon rubber shroud 24, protecting against contamination and leakage. The shroud is captive within an inward tubular extension 25 of the cap 2 and so is pulled off when that cap is removed just prior to use.

A plunger 26 is formed by a rod 27 and a piston 28 within the capsule 18. They are not connected: the piston is provided with the capsule 18, which may be filled with its charge and plugged by the piston quite separately from the assembly of the syringe. The rear end of the rod 27 is bifurcated and near the extreme end the resultant fingers are enlarged to form exterior shouldered abutments 29 against which the annular base of the drive member 8 acts. Near the root of the bifurcation there are further enlargements 30 on opposite sides with sloping surfaces which will wedge into the rear end of the capsule 18, as described below, to close the tips of the fingers together.

For use, the cap 2 is removed taking with it the shroud 24, and the cap 3 is turned through 90° from the "safe" position in FIG. 1, where the tab 5 is holding the hooks 12 apart and firmly engaged with the flange 11. The cap 3 is shown in the "use" position in FIGS. 2, 3 and 4. The device is then applied to where the injection is to be made and the centre of the cap 3 is pressed. The annulus 4 wedges the hooks 12 together and frees them from the flange 11. The spring 14 is then free to act and it shoots the drive member 8 forwards. The fluid in the capsule is virtually incompressible and it has a very narrow means of escape through the needle 22. The plunger 26 is therefore acting on a substantially solid body and it carries the capsule 18 forwards, compressing the spring 19. This action terminates as shown in FIG. 2, with the needle 18 projecting and the flange 20 hard up against the spacers 21.

With the capsule 18 arrested, the plunger 26 carries on under the influence of the dominant spring 14, forcing liquid out through the needle 22. As it reaches the end of the forward stroke (FIG. 3) the wedges 30 act to squeeze the bifurcated end of the rod 27 together, thus bringing the abutments 29 within the compass of the aperture at the base of the drive member 8. At this point, the drive member 8 is arrested by the rib 16, and so the spring 19 can then act, carrying the capsule 18 back with the rod 27 passing into the drive member 8 until the flange 20 abuts the forward side of the rib 16 (FIG. 4). This is the initial position of the capsule, and the needle is safe within the barrel.

Referring now to FIG. 5, a spring loaded drive member 31 acts on a plunger rod 32 through the intermediary of a toggle linkage 33. The toggles 34 and end discs 35 and 36 may be integrally moulded of plastics material with weaknesses at the hinge points. Initially, the toggles 34 are confined in a passage 37 so that they are virtually straight, as shown in full lines. However, towards the end of the forward stoke, the rear end of the rod 32 reaches an enlarged passage 38, and when the linkage 33 follows it is free to expand sideways as shown in broken lines. Thus, the thrust on the rod 32 is finished and the return spring acts on the plunger/capsule assembly. The rod 32 is urged rearwardly closing the two discs 35 and 36 together, this travel being sufficient to withdraw the needle.

Referring now to FIG. 6, a similar configuration of passages is used, with a narrow one 40 widening into an enlarged one 41. A drive member 42 has a cone 43 pointing forwards, its vertex engaging a ball 44 which is just slightly less in diameter than the passage 40. A similar cone 45 is at the rear end of a plunger rod 46, its vertex pointing to the rear also to engage the ball 44.

On the forward stroke the ball is restricted by the passage 40, and so transmits the thrust from the drive member 42 to the plunger rod 46. However, at the end of the forward stroke the coned end 45 enters the enlarged passage 41 and when it reaches the broken line position, the ball 44, which is in unstable captivity, falls away to one side, also as shown in broken lines. Thus the plunger, with the capsule, is free to return.

In order to facilitate construction and assembly, the barrel 1 may be made in two parts joined together after insertion of the capsule 18. The junction may conveniently be in the region of the rib 16.

In FIGS. 5 and 6, in order to achieve sufficient needle travel, the devices may have to be larger than that of FIGS. 1 to 4. But this can be alleviated to some extent by making those devices of flattened oval cross-section, the cross sections of the Figures being in the planes of the major axes.

Drugs are currently available pre-packaged in cartridges, similar to conventional syringes but with no end flanges. Such a cartridge has a cap with a pierceable rubber membrane at the reduced diameter delivery end which accepts a double-ended needle. This is packaged inside a shield which enables it to be fitted safely and easily, as well as giving it temporary protection. To provide a flange that would make it usable with the device described above, the cartridge may be fitted inside a sleeve-like carrier. This would be similarly contoured, with a neck surrounding the delivery end of the cartridge and an outwardly projecting flange performing the function of the flange 20 at the opposite end. The neck could be threaded to retain the needle.

We claim:

1. An injection device comprising a barrel, a drive member therein, a first spring means for urging the drive member towards a forward end of the barrel, a retaining mechanism for retaining the drive member at a rearward position in the barrel that can release the drive member and allow the member to move forwardly in the barrel under the first spring means urging said member forwardly within the barrel, a capsule within the barrel containing a liquid charge, second spring means for urging the capsule rearwardly, the second spring means being in opposition to but weaker in spring force than the first spring means, a needle connected with the capsule initially in a retracted position at the forward end of the barrel, a plunger with which said drive member co-operates to urge the plunger forwardly upon release of the drive member, a first phase of such forward movement driving the capsule and the needle to a position in which the needle projects beyond the barrel, and a second phase of such movement causing the plunger to eject the capsule charge through the needle, and means for decoupling the plunger from said drive member at the end of the second phase whereby the second spring means returns the capsule and needle to the needle retracted position, characterized in that for said first phase said drive member acts through the plunger and the liquid charge in the capsule to urge the capsule and needle forward, and in that the decoupling means is provided by the rear end of said plunger which is abutted by said drive member and which is adapted to be deformed when it comes into co-operation with the capsule to disengage from said drive member.

2. A device as claimed in claim 1, wherein said rear end of the plunger is bifurcated and there are exterior projections on fingers formed thereby, said projections, when engaged by the capsule on entry therein, causing the fingers to be wedged together and in constricted condition to be free to enter a passage within the drive member.

3. An injection device comprising a barrel, a drive member therein, a first spring means for urging the drive member towards a forward end of the barrel, a retaining mechanism for retaining the drive member at a rearward position in the barrel that can release the drive member and allow the member to move forwardly in the barrel under the first spring means urging said member forwardly within the barrel, a capsule within the barrel containing a liquid charge, a second spring means for urging the capsule rearwardly, the second spring means being in opposition to but weaker in spring force than the first spring means, a needle connected with the capsule initially in a retracted position at the forward end of the barrel, a plunger with which said drive member co-operates to urge the plunger forwardly upon release of the drive member, a first phase of such forward movement driving the capsule and the needle to a position in which the needle projects beyond the barrel, and a second phase of such movement causing the plunger to eject the capsule charge through the needle, and means for decoupling the plunger from said drive member at the end of the second phase whereby the second spring means returns the capsule and needle to the needle retracted position, characterized in that for said first phase said drive member acts through the plunger and the liquid charge in the capsule to urge the capsule and needle forward, and in that the decoupling means is provided by a thrust device between the rear end of the plunger and the forward end of the drive member, and a contoured passage within the barrel, the thrust device being maintained effectively rigid by confinement within a narrow portion of said passage for all but the final stage of the forward stroke, but being non-rigid when the confinement is eased by a wide portion of said passage for said final stage.

4. A device as claimed in claim 1 or 3, wherein the capsule is a proprietary syringe apart from said plunger.

5. A device as claimed in claim 1 or 3, wherein the spring means are coil springs co-axial within the barrel.

6. A device as claimed in claim 3, wherein said thrust device is an element that rolls free or otherwise escapes from between the plunger and the drive member when it attains lateral freedom of movement in said wide portion.

7. A device as claimed in claim 3, wherein said thrust device is a hinged linkage which is maintained substantially straight and extended by said narrow portion but which collapses sideways when it attains lateral freedom of movement in said wide portion.

* * * * *